US012714671B2

United States Patent
Campbell

(12) United States Patent
(10) Patent No.: US 12,714,671 B2
(45) Date of Patent: Aug. 25, 2026

(54) CELL MEMBRANE LIPID-EXTRACTED NANOPARTICLES (CLENs) FOR SELECTIVE TARGETING, IMAGE ANALYSIS AND CANCER THERAPY

(71) Applicant: Robert B. Campbell, Uxbridge, MA (US)

(72) Inventor: Robert B. Campbell, Uxbridge, MA (US)

( * ) Notice: Subject to any disclaimer, the term of this patent is extended or adjusted under 35 U.S.C. 154(b) by 733 days.

(21) Appl. No.: 17/262,292

(22) PCT Filed: Jul. 23, 2019

(86) PCT No.: PCT/US2019/042909
§ 371 (c)(1),
(2) Date: Jan. 22, 2021

(87) PCT Pub. No.: WO2020/023436
PCT Pub. Date: Jan. 30, 2020

(65) Prior Publication Data

US 2021/0338583 A1 Nov. 4, 2021

Related U.S. Application Data

(60) Provisional application No. 62/702,306, filed on Jul. 23, 2018.

(51) Int. Cl.

| | |
|---|---|
| ***A61K 9/1277*** | (2025.01) |
| ***A61K 9/1272*** | (2025.01) |
| ***A61K 31/704*** | (2006.01) |
| *B82Y 5/00* | (2011.01) |
| *B82Y 40/00* | (2011.01) |

(52) U.S. Cl.
CPC .......... *A61K 9/1277* (2013.01); *A61K 9/1272* (2013.01); *A61K 31/704* (2013.01); *B82Y 5/00* (2013.01); *B82Y 40/00* (2013.01)

(58) Field of Classification Search
CPC ............................ A61K 9/1277; A61K 9/1272
See application file for complete search history.

(56) References Cited

U.S. PATENT DOCUMENTS

| | | | | |
|---|---|---|---|---|
| 3,660,566 | A | 5/1972 | Vinson et al. | |
| 10,722,508 | B2 * | 7/2020 | Hong | A61P 3/04 |
| 2012/0164214 | A1 * | 6/2012 | Machluf | C12N 15/88 977/773 |
| 2013/0195765 | A1 | 8/2013 | Gho et al. | |
| 2013/0337066 | A1 * | 12/2013 | Zhang | A61K 9/148 424/234.1 |

OTHER PUBLICATIONS

Folch et al. (A Simple Method for the Isolation and Purification of Total Lipides from Animal Tissues, 1956) (Year: 1956).*
Buboltz et al. (A novel strategy for the preparation of liposomes: rapid solvent exchange, Biochimica et Biophysicia Acta, 1999) (Year: 1999).*
https://www.nanocs.net/DPPE-PEG5000.htm (Year: 2016).*
International Search Report and Written Opinion for Application No. PCT/US2019/042909 mailed Nov. 7, 2019.
International Preliminary Report on Patentability for Application No. PCT/US2019/042909 mailed Feb. 4, 2021.
Alharbi et al., Nano-formulations composed of cell membrane-specific cellular lipid extracts derived from target cells: physicochemical characterization and in vitro evaluation using cellular models of breast carcinoma. AAPS Open (2018) 4:5 https://doi.org/10.1186/s41120-018-0025-1.

* cited by examiner

*Primary Examiner* — Andrew S Rosenthal
*Assistant Examiner* — Danielle Kim

(57) ABSTRACT

Nanoliposome compositions and methods of making the same for selective targeting, image analysis and therapy (e.g., cancer therapy) are provided. In some aspects, the nanoliposomes comprise membrane material derived from cells (e.g., tumor cells) in order to selectively target agents (e.g., chemotherapeutic agents) to cancer cells. Membranes used to generate the nanoliposomes provided herein may be derived from cells in vivo, ex vivo, or in vitro. The disclosure also provides pharmaceutical compositions comprising nanoliposomes and methods of treatment by administering the same.

17 Claims, 4 Drawing Sheets

CELL MEMBRANE LIPID-EXTRACTED NANOPARTICLES (CLENs) FOR SELECTIVE TARGETING, IMAGE ANALYSIS AND CANCER THERAPY

RELATED APPLICATIONS

This application is a national stage filing under 35 U.S.C. § 371 of international application number PCT/US2019/042909, filed Jul. 23, 2019, which claims the benefit of priority under 35 U.S.C. § 119(e) of U.S. provisional application No. 62/702,306, filed Jul. 23, 2018, the entire contents of each of which are incorporated herein by reference.

FEDERALLY SPONSORED RESEARCH

This invention was made with government support under 1232339 awarded by the National Science Foundation CMMI. The government has certain rights in the invention.

BACKGROUND OF THE INVENTION

An important goal of chemotherapy is to eradicate the tumor mass while causing minimal side effects to the patient. Liposomes have been employed to help achieve this goal. The vesicle type has improved tumor targeting and when optimized can favorably alter the pharmacokinetic and biodistribution profile of the drug.(1-3) However, issues involving limited interstitial drug transport, off-target drug effects and formulation instability still remain.(2-4).

A current area of research investigation involves the development of nanomedicines capable of recognizing, and selectively targeting, exploitable tumor features for cancer therapy. (1, 3-6) A few advances in the field of nanoliposome development include the inclusion of poly-ethylene glycol (PEG)-PE in nano-size drug delivery systems (i.e., liposomes, micelles). (7) The liposome formulation product Doxil contains PEG, and as a result can successfully exploit the relatively large tumor vascular pore openings owing to extended circulation properties afforded by PEG. (6, 8-13) PEG has versatile functions. For example, its inclusion in cationic liposomes permits preferential tumor targeting, relatively longer circulation of cationic liposomes while significantly decreasing uptake by vessels in healthy tissues. (1, 5) Efforts to both gain access to and exploit the differential expression of various receptors in tumors for treatment when compared to normal tissues has improved with advances in liposome technology. (3, 4, 14) Such examples include the significant folate receptor-mediated uptake in athymic mice-bearing tumors overexpressing folate receptor-positive cells, compared to non-folate receptor-labeled systems for which reduced uptake was observed. (15) Accordingly, the development of nanomedicines capable of selectively targeting cells, e.g. cancer cells, is highly desired.

SUMMARY OF THE INVENTION

Some aspects of the disclosure are based on the recognition that using membrane lipids derived from cancer cells in the manufacture of liposomes is useful for targeting agents (e.g., chemotherapeutic agents) to cancer cells from which the membrane lipids were derived. Regardless of the specific variety of nanomedicine employed most drug delivery systems are prepared from natural and/or synthetic lipid ingredients. Moreover, the ratio of the ingredients employed rarely resemble the composition profile of the target cell membrane. In an effort to achieve more selective targeting cell membrane lipid-extracted nanoliposomes (CLENs) were designed, prepared and evaluated for use in vitro. The process involved the extraction of cellular lipid material from intended target cells, and the use of extracted lipid material with (and without) ingredients (e.g., cholesterol and/or PEG) for formulation and in vitro experimentation. Moreover, a single organ tissue environment was the primary focus of this investigation. The tissue model was additionally selected to represent an organ tissue environment for which the nano drug platform is being developed. For this reason, the cellular lipid material used to prepare CLENs was derived from breast tissue, except for when negative controls were employed.

The composition profile of extracted lipid components of CLENs more closely resemble the target cell membrane compared to non-specific preparations in terms of composition. For this reason, it was investigated whether CLENs prepared from lipid extracts derived from target cells will associate with the intended target cells to a greater extent when compared to CLENs prepared from non-specific lipid extracts, and/or conventional nanoliposomal preparations. Accordingly, some aspects of the disclosure provide a nanoliposome comprising (i) a membrane portion derived from a cell, and (ii) a chemotherapeutic agent. In some embodiments, the nanoliposome has a diameter ranging from 100 nm to 400 nm in diameter. In some embodiments, the nanoliposome has a diameter ranging from 150 nm to 300 nm. In some embodiments, the nanoliposome has a dimeter ranging from 150 nm to 263 nm. In some embodiments, the membrane portion is derived from the plasma membrane of the cell. In some embodiments, the cell is a cell from a cell line grown in cell culture. In some embodiments, the cell is from a cell line selected from the group consisting of 4T1, a BT-20, CRL-2089, SK-BR-3, and SK-OV-3.

It should be appreciated, that in some embodiments the cell is a cell (e.g., a tumor cell) obtained from a subject. In some embodiments, the subject has cancer. In some embodiments, the subject has breast cancer. In some embodiments, the cell is from a solid tumor. In some embodiments, the solid tumor is a breast tumor. In some embodiments, the subject has a blood cancer. In some embodiments, the cell is a leukemic cell. In some embodiments, the membrane portion of the cell is obtained via chloroform extraction. In some embodiments, the membrane portion of the cell is obtained via chloroform-methanol extraction.

In some embodiments, the nanoliposome comprises (e.g., within the lumen of the nanoliposome) a chemotherapeutic agent. In some embodiments, the chemotherapeutic agent is selected from the group consisting of alkylating agents, anthracyclines, cytoskeletal disruptors, epothilones, histone deacetylase inhibitors, topoisomerase I inhibitors, topoisomerase II inhibitors kinase inhibitors, nucleotide analogs, nucleotide precursor analogs, peptide antibiotics, platinum-based agents, retinoids, and vinca alkaloids. In some embodiments, the chemotherapeutic agent is doxorubicin.

It should be appreciated that the nanoliposome may comprise additional agents, for example agents that improve nanoliposome delivery. Accordingly, in some embodiments, the nanoliposome further comprises cholesterol. In some embodiments, the nanoliposome further comprises from 1 to 100 mol % of cholesterol. In some embodiments, the nanoliposome further comprises from 1 to 50 mol % of cholesterol. In some embodiments, the nanoliposome further comprises polyethylene glycol (PEG). In some embodiments, the PEG is DPPE-PEG-$_{5000}$. In some embodiments, the nanoliposome further comprises from 1 to 20 mol % of PEG. In some embodiments, the nanoliposome further comprises from 1 to 10 mol % of PEG.

Some aspects of the disclosure provide methods of making nanoliposomes. Accordingly, in some embodiments, the disclosure provides a method of making a nanoliposome comprising the steps of (i) isolating a cell membrane from a cell; and (ii) contacting the cell membrane isolated in (i) with a chemotherapeutic agent. In some embodiments, the cell membrane is isolated comprising chloroform extraction. In some embodiments, the cell membrane is isolated comprising chloroform-methanol extraction. In some embodiments, the cell membrane is a plasma cell membrane. In some embodiments, the method further comprises lyophilizing the cell membrane isolated in (i).

It should be appreciated that the methods provided herein embrace adding additional agents to the nanoliposomes provided herein, for example agents that improve nanoliposome delivery. Accordingly, in some embodiments, the method further comprises contacting the cell membrane with cholesterol. In some embodiments, from 1 to 100 mol % of cholesterol is contacted with the cell membrane. In some embodiments, from 1 to 50 mol % of cholesterol is contacted with the cell membrane. In some embodiments, the method further comprises contacting the cell membrane with polyethylene glycol (PEG). In some embodiments, the PEG is DPPE-PEG-$_{5000}$. In some embodiments, from 1 to 20 mol % of PEG is contacted with the cell membrane. In some embodiments, from 1 to 10 mol % of PEG is contacted with the cell membrane.

In some embodiments, the methods provided herein further comprise obtaining a cell from a subject, e.g. for the purposes of isolating membranes for the manufacture of nanoliposomes. In some embodiments, the subject has cancer. In some embodiments, the subject has breast cancer. In some embodiments, the cell is from a solid tumor. In some embodiments, the solid tumor is a breast tumor. In some embodiments, the subject has a blood cancer. In some embodiments, the cell is a leukemic cell. In other embodiments, the method further comprises obtaining the cell from a cell culture. In some embodiments, the cell is from a cell line selected from the group consisting of 4T1, a BT-20, CRL-2089, SK-BR-3, and SK-OV-3. In other aspects, the cell is an ex vivo cell grown in a cell culture.

The methods provided herein embrace contacting liposomes with one or more agents, e.g., chemotherapeutic agents. In some embodiments, the chemotherapeutic agent is selected from the group consisting of alkylating agents, anthracyclines, cytoskeletal disruptors, epothilones, histone deacetylase inhibitors, topoisomerase I inhibitors, topoisomerase II inhibitors kinase inhibitors, nucleotide analogs, nucleotide precursor analogs, peptide antibiotics, platinum-based agents, retinoids, and vinca alkaloids. In some embodiments, the chemotherapeutic agent is doxorubicin.

It should be appreciated that the methods provided herein further comprise administering the any of the nanoliposomes provided herein, to a subject. In some embodiments, the nanoliposome comprises a cell membrane from a tumor cell obtained from the subject. In some embodiments, the nanoliposome comprises a cell membrane from a tumor cell obtained from a different subject. Some aspects of the disclosure provide pharmaceutical compositions that comprise any of the nanoliposomes provided herein, or a nanoliposome produced by any of the methods provided herein. In some embodiments, the pharmaceutical composition comprises a pharmaceutically acceptable excipient.

Some aspects of the disclosure provide a method of treating a subject having a proliferative disease comprising: (i) obtaining a tumor cell from the subject; (ii) isolating a membrane from the tumor cell; (iii) contacting the membrane isolated in (ii) with a chemotherapeutic agent, thereby producing a nanoliposome comprising the chemotherapeutic agent; and (iv) administering the nanoliposome to the subject. In some embodiments, the tumor cell is from a solid tumor (e.g., a solid tumor obtained from the subject) In some embodiments, the proliferative disease is cancer. In some embodiments, the proliferative disease is breast cancer. In some embodiments, the subject is non-human. In some embodiments, the subject is human. In some embodiments, the nanoliposome of (iv) is administered intravenously. In some embodiments, the membrane isolated in (ii) is lyophilized. In some embodiments, the method further comprises contacting the membrane with cholesterol. In some embodiments, from 1 to 100 mol % of cholesterol is contacted with the membrane. In some embodiments, from 1 to 50 mol % of cholesterol is contacted with the membrane. In some embodiments, the method further comprises contacting the cell membrane with polyethylene glycol (PEG). In some embodiments, the PEG is DPPE-PEG-$_{5000}$. In some embodiments, from 1 to 20 mol % of PEG is contacted with the membrane. In some embodiments, from 1 to 10 mol % of PEG is contacted with the membrane.

DEFINITIONS

Figure 1:
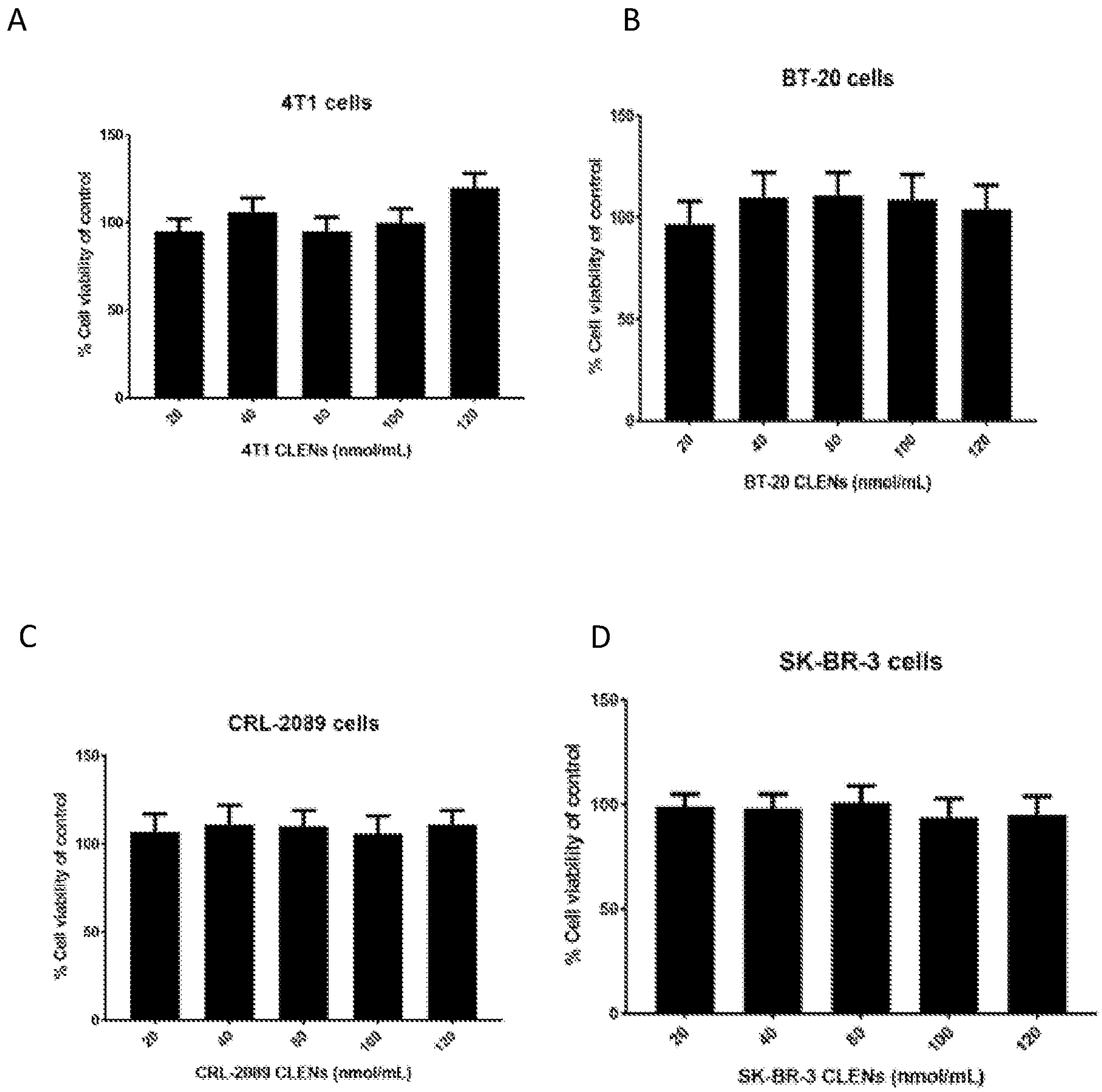
FIG. 1 shows an exemplary in vitro toxicity profile of CLENs. Cells were seeded at $1\times10^4$ cells/mL in a 48 well plate and incubated at 37° C. Percent of cell viability was determined following 24 h of exposure to 10 μmol/mL of respective CLENs. CLENs were added to plates seeded with the same cell line used in the general extraction and development of CLENs; (panel A) 4T1 cells were exposed to 4T1 CLENs, (panel B) BT-20 cells were exposed to BT-20 CLENs, (pane C) CRL-2089 cells were exposed to CRL-2089 CLENs and (panel D) SKBR-3 cells were exposed to SKBR-3 CLENs. Data are presented as mean±S.D; (n=6).

As used herein and in the claims, the singular forms "a," "an," and "the" include the singular and the plural reference unless the context clearly indicates otherwise. Thus, for example, a reference to "an agent" includes a single agent and a plurality of such agents.

As used herein, the term "nanoliposome" refers to a spherical vesicle having a least one lipid bilayer that is less than 1 μm in diameter. In some embodiments, the nanoliposome is from 10 nm to 950 nm in diameter. In some embodiments, the nanoliposome is from 10 nm to 800 nm in diameter. In some embodiments, the nanoliposome is from 10 nm to 600 nm in diameter. In some embodiments, the nanoliposome is from 10 nm to 500 nm in diameter. In some embodiments, the nanoliposome is from 50 to 500 nm in diameter. In some embodiments, the nanoliposome is from 100 to 400 nm, (e.g., about 150, about 158 nm, about 263 nm, about 187 nm, about 203 nm, or about 200 nm in diameter).

As used herein, the term "cell membrane lipid extracted nanoliposome" or "CLEN" refers to a nanoliposome in which at least a portion of its lipid bilayer is derived from a cell (e.g. a tumor cell). In some embodiments, at least 10%, 20%, 30%, 40%, 50%, 60%, 70%, 80%, 90%, 95%, 98% or at least 99% of the CLEN is comprised of a lipid bilayer from a cell. In some embodiments, the CLEN comprises a lipid bilayer from a tumor cell, such as a tumor cell that was obtained from a solid tumor from a subject.

As used herein, the term "approximately" or "about," as applied to one or more values of interest, refers to a value that is similar to a stated reference value. In certain embodiments, the term "approximately" or "about" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (for example, when such number would exceed 100% of a possible value).

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe).

As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

As used herein, the term "therapeutically effective amount" means an amount of an agent to be delivered (e.g., nucleic acid, protein, drug, therapeutic agent, diagnostic agent, prophylactic agent, chemotherapeutic agent etc.) that is sufficient, when administered to a subject suffering from or susceptible to a disease, disorder, and/or condition, to treat, improve symptoms of, diagnose, prevent, and/or delay the onset of the disease, disorder, and/or condition.

As used herein, the term "treating" refers to partially or completely preventing, and/or reducing incidence of one or more symptoms or features of a particular disease or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, or condition for the purpose of decreasing the risk of developing more severe effects associated with the disease, or condition.

As used herein, the term "agent" refers to a molecule, e.g., a small molecule, lipid, carbohydrate, protein, or nucleic acid that is capable of being incorporated into a nanoliposome.

As used herein, the term "chemotherapeutic agent" refers to an agent known in the art to be of use in chemotherapy for cancer. Exemplary chemotherapeutic agents include, without limitation, alkylating agents (e.g., Cyclophosphamide, Mechlorethamine, Chlorambucil, Melphalan, Dacarbazine, Nitrosoureas, and Temozolomide), anthracyclines (e.g., Daunorubicin, Doxorubicin, Epirubicin, Idarubicin, Mitoxantrone, and Valrubicin), cytoskeletal disruptors (e.g., Paclitaxel, Docetaxel, Abraxane, and Taxotere), epothilones (e.g., epothilone), histone deacetylase inhibitors (e.g., Vorinostat, and Romidepsin), topoisomerase I inhibitors (e.g., Irinotecan, and Topotecan), topoisomerase II inhibitors (e.g., Etoposide, Teniposide, and Tafluposide), kinase inhibitors (e.g., Bortezomib, Erlotinib, Gefitinib, Imatinib, Vemurafenib, and Vismodegib), nucleotide and nucleotide precursor analogs (e.g., Azacitidine, Azathioprine, Capecitabine, Cytarabine, Doxifluridine, Fluorouracil, Gemcitabine, Hydroxyurea, Mercaptopurine, Methotrexate, and Tioguanine), peptide antibiotics (e.g., Bleomycin, and Actinomycin), platinum-based agents (e.g., Carboplatin, Cisplatin, and Oxaliplatin), retinoids (e.g., Tretinoin, Alitretinoin, and Bexarotene), and vinca alkaloids (e.g., Vinblastine, Vincristine, Vindesine, and Vinorelbine).

As used herein, the term "proliferative disease," refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasia is also referred to as cancer. Exemplary proliferative diseases include, without limitation, Acute Lymphoblastic Leukemia (ALL), Acute Myeloid Leukemia (AML), Adrenocortical Carcinoma, Childhood Adrenocortical Carcinoma, Kaposi Sarcoma, AIDS-Related Lymphoma, Primary CNS Lymphoma, Anal Cancer, Appendix Cancer, Astrocytomas, Atypical Teratoid/Rhabdoid Tumor, Basal Cell Carcinoma of the Skin, Bile Duct Cancer, Bladder Cancer, Bone Cancer (includes, e.g., Ewing Sarcoma and Osteosarcoma and Malignant Fibrous Histiocytoma), Brain Tumors, Breast Cancer, Bronchial Tumors, Burkitt Lymphoma, Carcinoid Tumor, Cardiac (Heart) Tumors, Atypical Teratoid/Rhabdoid Tumor, Embryonal Tumors, Germ Cell Tumor, Primary CNS Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma, Ductal Carcinoma In Situ (DCIS), Embryonal Tumors, Endometrial Cancer (Uterine Cancer), Ependymoma, Esophageal Cancer Esthesioneuroblastoma (Head and Neck Cancer), Ewing Sarcoma (Bone Cancer), Extracranial Germ Cell Tumor, Extragonadal Germ Cell Tumor, Eye Cancer, Childhood Intraocular Melanoma, Intraocular Melanoma, Retinoblastoma, Fallopian Tube Cancer, Fibrous Histiocytoma of Bone, Gallbladder Cancer, Gastric (Stomach) Cancer, Gastrointestinal Carcinoid Tumor, Gastrointestinal Stromal Tumors (GIST), Germ Cell Tumors, Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Histiocytosis, Langerhans Cell, Hodgkin Lymphoma, Hypopharyngeal Cancer (Head and Neck Cancer), Intraocular Melanoma, Islet Cell Tumors, Pancreatic Neuroendocrine Tumors, Kidney (Renal Cell) Cancer, Langerhans Cell Histiocytosis, Laryngeal Cancer (Head and Neck Cancer), Leukemia, Lip and Oral Cavity Cancer (Head and Neck Cancer), Liver Cancer, Lung Cancer (Non-Small Cell and Small Cell), Lymphoma, Male Breast Cancer, Malignant Fibrous Histiocytoma of Bone and Osteosarcoma, Melanoma, Intraocular (Eye), Merkel Cell Carcinoma (Skin Cancer), Mesothelioma, Malignant, Metastatic Cancer, Metastatic Squamous Neck Cancer with Occult Primary (Head and Neck Cancer), Midline Tract Carcinoma With NUT Gene Changes, Mouth Cancer (Head and Neck Cancer), Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Myelogenous Leukemia, Chronic (CML), Myeloid Leukemia, Acute (AML), Myeloproliferative Neoplasms, Chronic, Nasal Cavity and Paranasal Sinus Cancer (Head and Neck Cancer), Nasopharyngeal Cancer (Head and Neck Cancer), Neuroblastoma, Non-Hodgkin Lymphoma, Non-Small Cell Lung Cancer, Oral Cancer, Lip and Oral Cavity Cancer and Oropharyngeal Cancer (Head and Neck Cancer), Osteosarcoma and Malignant Fibrous Histiocytoma of Bone, Ovarian Cancer, Pancreatic Cancer, Pancreatic Neuroendocrine Tumors (Islet Cell Tumors), Papillomatosis (Childhood Laryngeal), Paraganglioma, Childhood Paraganglioma—see Unusual Cancers of Childhood, Paranasal Sinus and Nasal Cavity Cancer (Head and Neck Cancer), Parathyroid Cancer, Penile Cancer, Pharyngeal Cancer (Head and Neck Cancer), Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Prostate Cancer, Rectal Cancer, Recurrent Cancer, Renal Cell (Kidney) Cancer, Retinoblastoma, Rhabdomyosarcoma, Childhood (Soft Tissue Sarcoma), Salivary Gland Cancer (Head and Neck Cancer), Sarcoma, Ewing Sarcoma (Bone Cancer), Osteosarcoma (Bone Cancer), Soft Tissue Sarcoma, Uterine Sarcoma, Sézary Syndrome (Lymphoma), Skin Cancer, Small Cell Lung Cancer, Small Intestine Cancer, Soft Tissue Sarcoma, Squamous Cell Carcinoma of the Skin, Squamous Neck Cancer with Occult Primary, Metastatic (Head and Neck Cancer), Stomach (Gastric) Cancer, T-Cell Lymphoma, Cutaneous (Mycosis Fungoides and Sezary Syndrome), Testicular Cancer, Throat Cancer (Head and Neck Cancer), Nasopharyngeal Cancer, Oropharyngeal Cancer, Hypopharyngeal Cancer, Thymoma and Thymic Carcinoma, Thyroid Cancer, Transitional Cell Cancer of the Renal Pelvis and Ureter (Kidney (Renal Cell) Cancer), Ureter and Renal Pelvis, Transitional Cell Cancer (Kidney (Renal Cell) Cancer, Urethral Cancer, Uterine Cancer, Endometrial, Uterine Sarcoma, Vaginal Cancer, Vascular Tumors (Soft Tissue Sarcoma), Vulvar Cancer, and Wilms Tumor. A skilled artisan would appreciate that cell membranes may be isolated for cells of any of the above cancer types in order to make any of the nanoliposomes provided herein.

As used herein, the term "nucleic acid" and "nucleic acid molecule," refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, e.g., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Abbreviations

CLENs Cell membrane lipid extracted nanoliposomes
DOPG 1, 2-dioleoyl-Sn-glycero-3-[phospho-rac-(1-glycerol)]
DOPC 1,2-Dioleoyl-sn-Glycero-3-Phosphocholine
Chol Cholesterol
DPPE-PEG-$_{5000}$ 1,2-dipalmitoryl-sn-glycero-3-[phospho-ethanolamine (PEG)]-5000
Rhodamine-DPPE 1,2-dipalmitoyl-sn-glycero-3-phosphoethanolamine-N-(Lissamine rhodamine B sulfonyl)
SRB Sulforhodamine B
TCA Trichloroacidic acid
Doxil Stealth liposomal doxorubicin
Doxil$_{LP}$ Doxil lipid preparation only (no drug loaded)
SC-GSLs Short-chained glycosphingolipids

DETAILED DESCRIPTION OF THE INVENTION

The instant disclosure relates to the discovery that nanoliposomes that include membranes derived from tumor cells are effective for selectively delivering agents (e.g., chemotherapeutic agents) to tumor cells. Furthermore, addition of additional agents to the nanoliposomes, such as cholesterol and/or PEG can improve delivery of agents, such as chemotherapeutic agents, to tumor cells.

Highly selective drug targeting is an important goal in the development of nanotechnologies, including cancer nanotechnologies. To improve tumor targeting methods and compositions were developed to formulate cell membrane lipid-extracted nanoliposomes (CLENs). The formulations included components extracted from the membrane of cancer cells, e.g., cancer cells to be targeted by CLENs. Examples provided herein describe three different breast cancer cell lines (4T1, BT-20, and SK-BR-3). As controls for normal breast and cancer tissue environments normal breast fibroblast (CRL-2089) and ovarian cancer (SK-OV-3) cell lines were employed, respectively. Physicochemical properties, efficiency of drug loading, cellular uptake, and cytotoxicity were evaluated. The mean diameter and zeta potential values for the 5 different CLENs were 202±38 nm and −15±3.8 my, respectively. Doxorubicin hydrochloride (5 mol %) increased the size of 4T1-CLENs from 158±2 nm to 212±59 nm, with no significant change in the negatively-charged surface potential. Percent of drug loaded ranged from 40 to 93%, varying according to the ratio of lipid extract to conventional components employed. The additional inclusion of cholesterol and DPPE-PEG5000 increased drug loading in CLENs, similar to Doxil preparations. Promising cellular uptake and cytotoxicity profiles were observed when the lipid ingredients were derived from the eventual target cell. Given the ability of CLENs to better recognize target cells compared to nanosystems consisting of non-specific lipid extracts or conventional liposome ingredients alone, CLENs have demonstrated early promise as a nano-delivery systems for cancer treatment.

Pharmaceutical Compositions

Any of the nanoliposomes (e.g., CLENs) described herein can be mixed with a pharmaceutically acceptable carrier to form a pharmaceutical composition for use, e.g., in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. See, e.g., Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some examples, the pharmaceutical composition described herein comprises nanoliposomes containing one or chemotherapeutic agents, which can be prepared by methods, such as those described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes may extruded through filters of defined pore size to yield liposomes with the desired diameter. In some embodiments, lipids for making nanoliposomes are extracted as described in Bligh and Dyer method (17), the entire contents of which are hereby incorporated by reference.

The nanoliposomes may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the nanoliposomes which matrices are in the form of shaped articles, e.g. films, or microcapsules. Examples of sustained-release matrices include polyesters, hydrogels (for example, poly(2-hydroxyethyl-methacrylate), or poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic nanoliposomes (e.g., CLENs) may be placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0.

The emulsion compositions can be those prepared by mixing nanoliposomes (e.g., CLENs) with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Methods of Treatment

Any of the nanoliposomes (e.g., CLENs) described herein can be used to in treating a proliferative disease, such as cancer.

To practice the method disclosed herein, an effective amount of the pharmaceutical composition described herein that contains at least one nanoliposome (e.g., CLEN) can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the nanoliposomes (e.g., CLENs) described herein can be aerosolized using a fluorocarbon formulation and a metered dose inhaler, or inhaled as a lyophilized and milled powder.

In some embodiments, the therapeutic effect is reduced tumor burden, or reduction of cancer cells. Determination of whether an amount of the nanoliposomes (e.g., CLENs) achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder. Alternatively, sustained continuous release formulations of a nanoliposomes (e.g., CLENs) may be appropriate. Various formulations and devices for achieving sustained release are known in the art.

In one example, dosages for a nanoliposome (e.g., CLEN) as described herein may be determined empirically in individuals who have been given one or more administration(s) of the nanoliposome (e.g., CLEN). Individuals are given incremental dosages of the antagonist. To assess efficacy of the antagonist, an indicator of the disease/disorder can be followed.

In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen can vary over time.

In some embodiments, the nanoliposomes (e.g., CLENs) described herein are administered to a subject in need of the treatment at an amount sufficient to reduce tumor burden or cancer cell growth, by at least 5% (e.g., 10%, 20%, 30%, 40%, 50%, 60%, 70%, 80%, 90% or greater) in vivo.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, nanoliposomes (e.g., CLENs) can be administered by the drip method, whereby a pharmaceutical formulation containing the nanoliposomes (e.g., CLENs) and physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the nanoliposomes (e.g., CLENs), can be dissolved and administered in a pharmaceutical excipient such as Water-for-Injection, 0.9% saline, or 5% glucose solution.

In one embodiment, a nanoliposome (e.g., CLEN) is administered via site-specific or targeted local delivery techniques. Examples of site-specific or targeted local delivery techniques include various implantable depot sources of nanoliposomes (e.g., CLENs) or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

The subject to be treated by the methods described herein can be a mammal, such as a farm animals, sport animals, pets, primates, horses, dogs, cats, mice and rats. In one example, the subject is a human. Nanoliposomes (e.g., CLENs) may be used for targeting chemotherapeutic agents to cancer cells. In some examples, the subject may be a human patient having, suspected of having, or at risk for a cancer, such as breast cancer, prostate cancer, liver cancer, lung cancer, melanoma, colorectal cancer, or renal-cell cancer. Such a patient can also be identified by routine medical practices.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Example 1: Nano-formulations composed of cell membrane-specific cellular lipid extracts derived from target cells: Physiochemical characterization and in vitro evaluation using cellular models of breast carcinoma.

Materials and Methods

Materials

The lipids 1, 2-dioleoyl-Sn-glycero-3-[phospho-rac-(1-glycerol)] (DOPG), 1,2-dioleoyl-sn-glycero-3-phosphocholine (DOPC), Cholesterol (Chol), 1,2-dipalmitoryl-sn-glycero-3-[phospho-ethanolamine (Polyethylene glycol)]-5000 (DPPE-$PEG_{5000}$), 1,2-dipalmitoyl-sn-glycero-3-phosphoethanolamine-N- (lissamine rhodamine B sulfonyl) (rhodamine-$_{DPPE}$), were purchased from Avanti Polar Lipids (Alabaster, AL). Sulforhodamine B (SRB) and Doxorubicin hydrochloride (98% HPLC) were purchased from Sigma-Aldrich (St Louis, MO). All chemicals and solvents used in this study were of analytical grade and obtained from Fisher Scientific (Pittsburgh, PA).

Cell Culture

Human breast cancer cell lines BT-20 (HTB-19), SKBR3 (HTB-30), murine mammary cell line 4T1 (CRL-2539), normal mammary fibroblast cell line CCD-1069SK (CRL-2089), and ovarian cancer cell line SK-OV-3 (HTB-77) were obtained from ATCC (American Type Culture Collection, Manassas, VA). All cell line cultures were grown in a humidified atmosphere of 5% $CO_2$ at 37° C.

Cellular Lipid Extraction

Method used to extract the cellular lipid material were modified from the original Bligh and Dyer method established in 1959.(17) The standard gravimetric quantification method involves the use of three different solvents. In brief, when cells reached approximately 90% confluence, they were trypsinized and collected. The pellet of cells was diluted with 1×PBS (phosphate buffer saline). The average number of cells in a pellet determined the proportion of solvents used according to a modified chart (Table 1). Three solvents were added step-wise as follows: 1:2 chloroform-methanol mixture, chloroform, and distilled water, vortexed intermittently between solvent additions. The final mixture was centrifuged at 1000 rpm at 4° C. for 5 minutes to obtain a two-phased system; the bottom lipid layer was aspirated and transferred into a glass tube and refrigerated until a sufficient volume was obtained.

TABLE 1

Modified chart of the Dyer and Bligh lipid extraction method.

| Cell Number (millions) | (5-9.9) | (10-24.9) | (25-49.9) | (50-74.9) | (75-99.9) |
|---|---|---|---|---|---|
| 1:2 $CHCl_3$:MeOH | 0.750 | 1.9 | 3.75 | 5.7 | 7.5 |
| $CHCl_3$ | 0.250 | 0.625 | 1.25 | 1.875 | 2.5 |
| $dH_2O$ | 0.250 | 0.625 | 1.25 | 1.875 | 2.5 |
| Total Volume | 1.45 | 3.65 | 7.25 | 10.95 | 14.50 |

Lyophilization Method

Extracted lipids were dehydrated to form a film using a rotary evaporator system, and a heating bath (Buchi B-491) (Flawil, Switzerland) with temperatures maintained at 40-50° C. Sucrose (0.2 M) was added to serve as a cryoprotectant during the process of lyophilization using a FreeZone Freeze Dry system (Labconco, Kansas City, MO). The lipid powder was weighed and subsequently dissolved in 1 mL of chloroform. All lipid chloroform stocks used to prepare CLENs were stored at −80° C. Prior to using the lipid extracts for preparation of CLENs batches of the freeze dried lipid extract were evaluated by LCMS. All lipid components were identified, and the relative abundance and molecular weights for each lipid extract type was determined, resulting in average molecular weights. The final concentrations were subsequently determined for the lipid extract stocks and later used to prepare CLENs in absence and presence of drug agents.

CLENs and Conventional Liposome Preparations

CLENs used in this study were generally derived from breast cancer cell lines. CLENs were named by the cell line from which the lipid material was derived (i.e., 4T1 CLENs, BT-20 CLENs etc.). The composition of nanoliposome formulations employed was as follows: $Doxil_{LP}$ comprised of DSPC/chol/PEG-$_{5000}$ (50/45/5). 4T1 CLENs were employed with the inclusion of chol (0, 10, 25, or 50 mol %) and DPPE-$PEG_{5000}$ (0, 2, 5, or 10 mol %). When necessary, rhodamine-$_{DPPE}$ label was included in CLENs at the ratio of 1 mol %. CLENs were prepared by thin film hydration method as previously reported (1, 18-20). Particle size and zeta (0 potential were determined following five minutes of sonication using a 90 Plus Particle/Zeta Potential Analyzer (Brookhaven Instruments, Holtsville, NY).

Drug Incorporation Efficiency

Doxorubicin hydrochloride (5 mol %) was loaded in conventional and 4T1 CLENs. To determine drug incorporation efficiency, the two fractions (incorporated and unincorporated free drug) were separated. First, a required volume was removed from each preparation type and stored at 4° C. Next, each preparation was centrifuged using an ultra-centrifugation system at 13,000 rpm for 15 minutes, and a pre-determined volume was removed from the preparation and stored at 4° C. The centrifuged formulation was transferred to a Float-A-lyzer system with 1000 MW semi-permeable membrane (Fisher Scientific, Pittsburgh, PA) and placed in a beaker filled with 1×PBS at 4° C. overnight. The next day, a required volume from the dialyzed formulation was removed and used for analysis. The three samples (before centrifugation, after centrifugation, and after dialysis) were added to a 96-well plate to determine doxorubicin fluorescence intensity using a fluorescence microplate reader. The fluorescence intensity was measured at excitation and emission wavelengths of 540/20 nm and 590/20 nm, respectively.

The percentage of doxorubicin incorporated was calculated using the following equation:

$$\text{Percent of drug Incorporated} = \frac{\text{Fluorescence intensity (after dialysis sample)}}{\text{Fluorescence intensity (before dialysis sample)}} \times 100$$

Cellular Uptake Studies

Cells were seeded at $1\times10^4$/mL in a 48-well plate and incubated at 37° C. Following 24 hours of incubation, rhodamine labelled CLENs prepared from specific cell lines were added to the respective well at different concentrations. Following an additional 24 hours of incubation the plates were washed with 1×PBS and analysed using a fluorescence microplate reader (BioTek Instruments, Winooski, Vermont).

Cytotoxicity of Doxorubicin-Loaded CLENs

Sulforhodamine B (SRB) assay was used to determine percent viability of control based on the amount of basic proteins in viable cells following exposure to different CLENs. Cells were seeded at $1\times10^4$ per ml in a 48-well plate. Columns of cells in the 48 well plate were exposed to either doxil, free doxorubicin, SKBR-3, BT-20 or 4T1 CLENs-loaded with doxorubicin (5 mol %). Following a 24 h incubation period at 37° C., cells were treated with various concentrations of different types of CLENs loaded with doxorubicin HCl. The following day, SRB assay was utilized to determine the percent of cell viability. Briefly, plates were washed twice with 1×PBS and the cells were fixed with 50% wt/vol TCA (Trichloroacetic acid) and stored at 4° C. for 1 hour. Next, plates were washed five times by distilled deionized water, stained by 0.4% w/v of SRB dye, and placed in the dark for 30 minutes. Excess dye was washed minimum of four times with 1% v/v acetic acid and left to dry completely. Finally, 1 mL of 1×PBS was added to each well and the plate was analyzed using a fluorescence microplate reader. The fluorescence intensity was measured at excitation wavelength of 540/20 nm and emission wavelength of 590/20 nm using FLX 800 Fluorescence Microplate Reader (Bio-tech Instruments, Winooski, VT).

Cellular Toxicity of CLENs:

To determine the level of cellular toxicity of CLENs compared to controls the Sulforhodamine B (SRB) assay was performed as reported elsewhere (17-19), and as briefly described under the section cytotoxicity of doxorubicin-loaded CLENs.

Statistics

Statistical analysis was performed using ANOVA (analysis of variance) followed by Turkey's multiple comparison procedure as post-hoc, and two-tailed Student's t-test using Sigma Plot for Windows (Systat Software, San Jose, CA). Results are presented as mean±SD, n=6. $P<0.05$ and $P<0.001$ were considered statistically significant and denoted as * and **, respectively.

Results: Characterization of CLENs

The physicochemical properties such as particle size and surface charge potential are important to assess the quality of the preparation, including drug incorporation, stability and drug release characteristics. Particle size and zeta (ζ) potential of the different CLENs were determined using the PALS zeta potential analyzer. The unimodal particle size distribution ranged between 150 and 263 nm, with an increase in size observed for preparations including cholesterol and DPPE-PEG-$_{5000}$. All preparations exhibited negative zeta potential values ranging between −11 to −21 mV (Table 2).

TABLE 2

Characterization of different CLENs developed from breast cells.

| # | Nanoliposomal Preparations | Particle Size (nm) | Zeta potential (mV) |
|---|---|---|---|
| 1 | Doxil$_{LP}$ | 150 ± 2.0 | −23 ± 0.9 |
| 2 | 4T1 CLENs | 158 ± 1.9 | −17 ± 2.5 |
| 3 | BT-20 CLENs | 263 ± 1.4 | −21 ± 3.5 |
| 4 | SK-BR-3 CLENs | 187 ± 2.1 | −13 ± 1.1 |
| 5 | CRL-2089 CLENs | 203 ± 1.9 | −15 ± 1.3 |
| 6 | SK-OV-3 CLENs | 200 ± 2.2 | −11 ± 2.3 |

Incorporation Efficiency of Doxorubicin in 4T1-CLENs

The percent of drug incorporated in a drug carrier molecule is an important step in formulation development. For this reason, the incorporation efficiency for doxorubicin in 4T1-CLENs was evaluated (Table 3). The inclusion of 25 mol % cholesterol, and DPPE-PEG-$_{5000}$ (2 or 5 mol %) in 4T1-CLENs demonstrated the best results. Drug incorporation was similar to the incorporation of doxorubicin in Doxil (Table 3). The incorporation of the drug increased the size of 4T1-CLENs, with no observable effect on the values for zeta potential.

TABLE 3

Characterization and evaluation of 4T1 CLENs loading efficiency.

| # | Nanoliposomes | mol % | Particle Size (nm) | Z-Potential (mV) | Dox Incorporation Efficiency % |
|---|---|---|---|---|---|
| 1 | 4T1/chol | 100/0 | 131 ± 6.5 | −14 ± 0.4 | 63 ± 1.3 |
| 2 | 4T1/chol | 90/10 | 184 ± 0.4 | −20 ± 1.2 | 64 ± 1.9 |
| 3 | 4T1/chol | 75/25 | 239 ± 4.3 | −18 ± 2.50 | 86 ± 0.9 |
| 4 | 4T1/chol | 50/50 | 282 ± 0.3 | −20 ± 2.50 | 44 ± 0.9 |
| 5 | 4T1/chol/PEG-$_{5000}$ | 73/25/2 | 180 ± 5.2 | −10 ± 1.2 | 81 ± 1.5 |
| 6 | 4T1/chol/PEG-$_{5000}$ | 70/25/5 | 179 ± 0.2 | −13 ± 1.5 | 93 ± 0.9 |
| 7 | 4T1/chol/PEG-$_{5000}$ | 65/25/10 | 290 ± 0.4 | −10 ± 1.7 | 41 ± 0.3 |
| 8 | Doxil$_{LP}$ | 45/50/5 | 168 ± 0.6 | −13 ± 1.5 | 95 ± 1.1 |

In Vitro Cellular Toxicity Profile of CLENs

The SRB assay was performed for different preparations of CLENs and compared to the relative effects of conventional liposomes. The toxicity profile was determined for four different cell lines: three mammary epithelial (4T1, BT-20, SK-BR-3), and one mammary fibroblast (CRL-2089). Each cell line variety was exposed to five different types of CLENs. A toxicity profile for each preparation is shown in FIG. 1. All CLENs demonstrated a relatively non-toxic effect against cellular growth within the concentration range evaluated. In comparison to the untreated control minimal toxicity was observed for CLENs. CLENs demonstrated similar toxicity profiles compared to doxil$_{LP}$ (data not shown).

Cellular Uptake of CLENs

Figure 2:
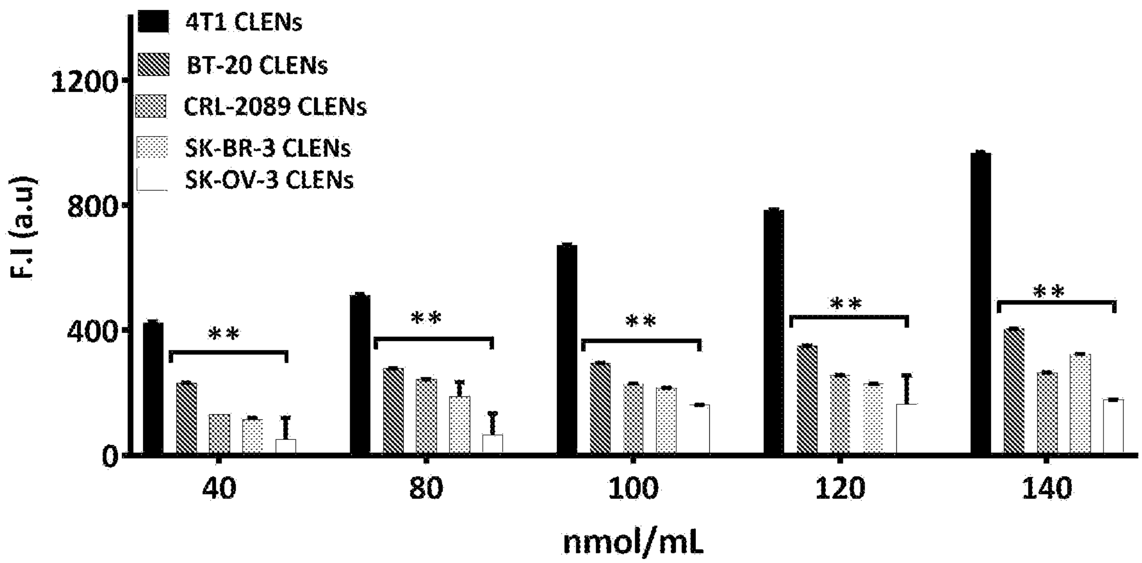
FIG. 2 shows exemplary 4T1 cellular uptake studies. An amount of $1\times10^4$ 4 T1 cells were seeded in a 48 well plate. After 24 hours, cells were exposed to different concentration of fluorescently labeled CLENs and incubated with the cells for an additional 24 hours. The most significant cellular uptake was observed with 4T1 cells compared to the other breast cells. The least amount of cellular uptake was observed with the ovarian cancer (negative control) cell line, SK-OV-3. Data are presented as mean±S.D; (n=6).
Figure 3:
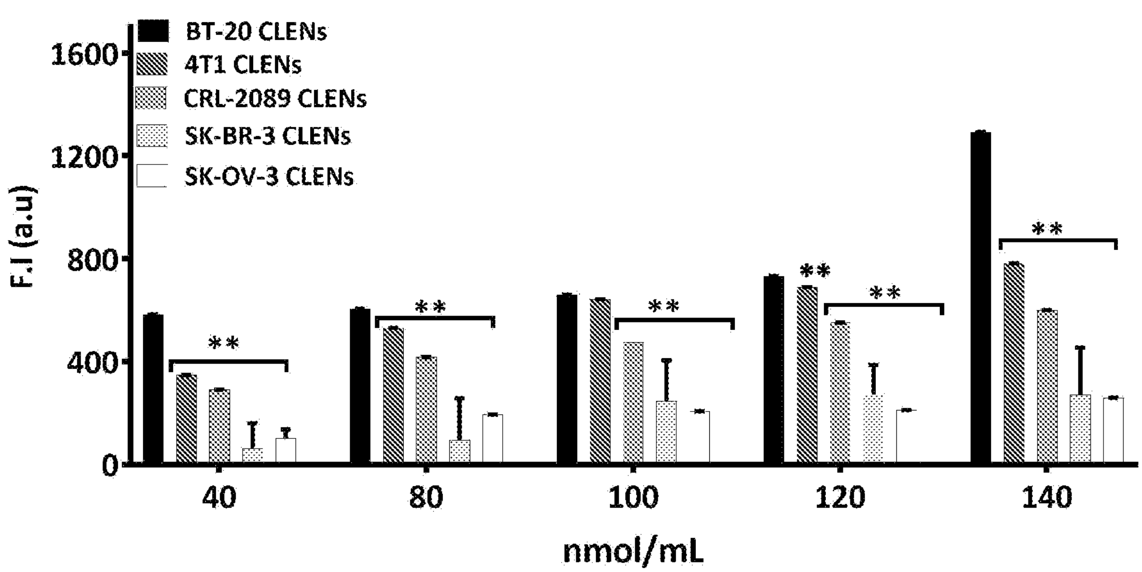
FIG. 3 shows exemplary BT-cellular uptake studies. An amount of 1×104 BT-20 cells were seeded in a 48 well plate. After 24 h, cells were exposed to different concentrations of fluorescently labeled CLENs for 24 h. The data show cellular uptake of CLENs by all the cells, with the highest degree of uptake observed with BT-20 cells, and the least amount of cellular uptake was observed with the (negative control) ovarian cancer cell line, SK-OV-3. Data are presented as mean±S.D; (n=6).
Figure 4:
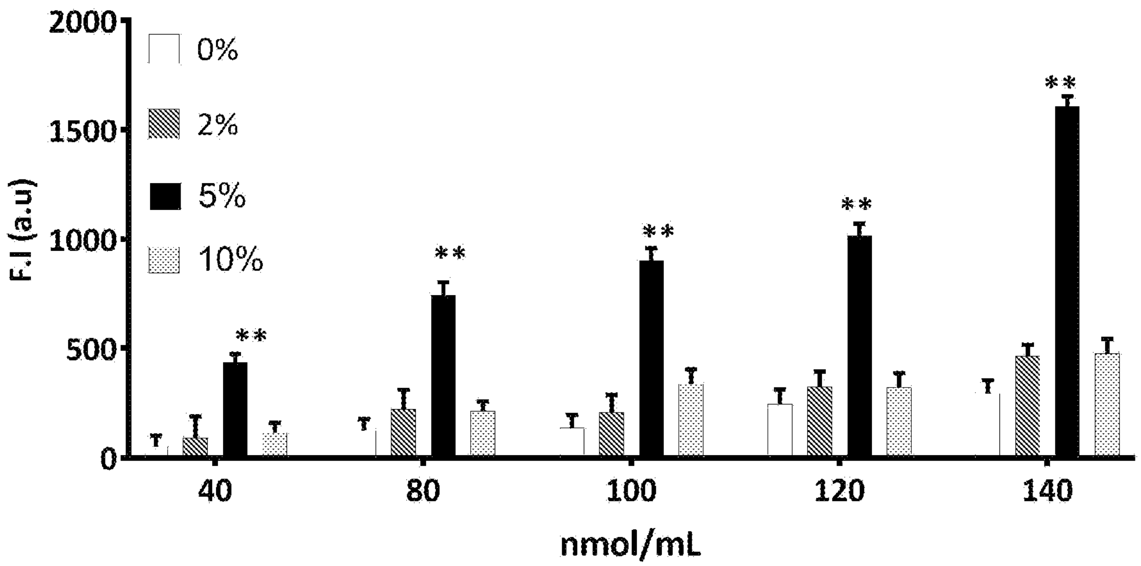
FIG. 4 shows exemplary effects of cholesterol and PEG inclusion on cellular uptake of CLENs. Four different preparations of 4T1 CLENs containing 25 mol % of cholesterol and different mol % of DPPE-PEG-$_{5000}$ (0, 2, 5 and 10%) were evaluated for cellular uptake against 4T1 cell line. Rhodamine-labeled CLENs were used for this study. The cells were seeded in a 48-well plate followed by the addition of CLENs for 24 hours. The fluorescence intensity used here as an indicator of cell uptake was measured using a fluorescence microplate reader. CLENs containing 5 mol % of DPPE-PEG-$_{5000}$ demonstrated the most significant uptake compared to other varieties within the concentration range employed. Data are presented as mean±S.D; (n=6).
Figure 5:
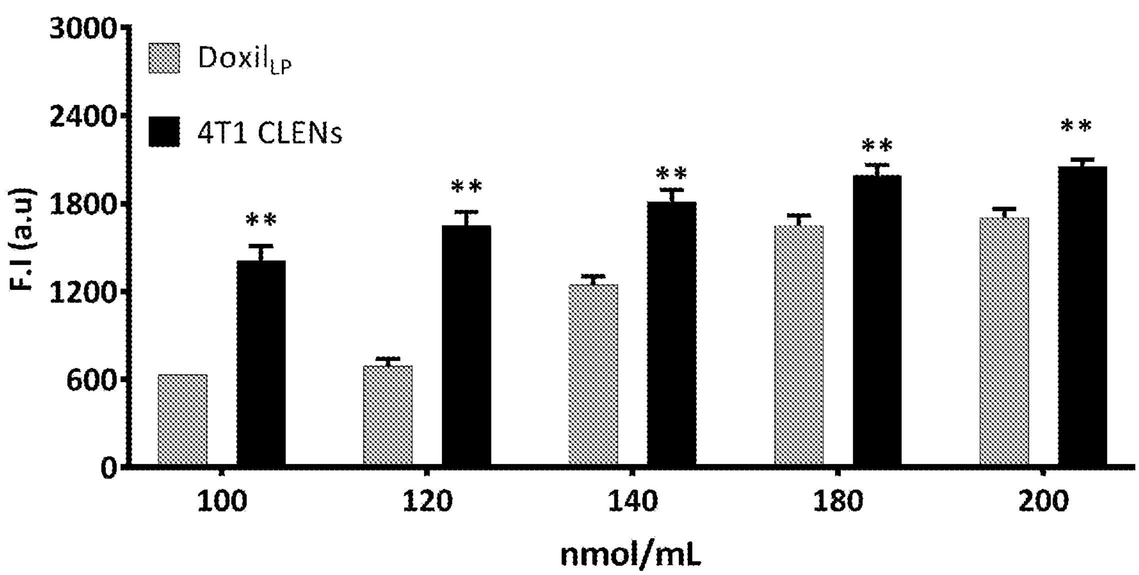
FIG. 5 shows exemplary comparisons of cellular uptake of CLENs and Doxil$_{LP}$. An amount of $1\times10^4$ 4 T1 cells were seeded in a 48-well plate. After 24 h, cells were incubated for an additional 24 h with various concentrations of rhodamine labeled CLENs (containing 5 mol % of PEG-$_{5000}$) and Doxil$_{LP}$. The data show that CLENs containing 5 mol % of DPPE-PEG-$_{5000}$ were taken up to a greater extent compared to the conventional Doxil$_{LP}$. Error bars indicate mean±S.D. (n=6).

Cellular uptake studies were performed to determine the extent to which CLENs were taken up by various breast cancer cell lines. FIG. 2 showed significant cellular uptake of CLENs when 4T1 cells were exposed to 4T1 CLENs, compared to other CLEN varieties. Similar results were observed for when the BT-20 cell line was exposed to BT-20 CLENs (FIG. 3). Minimal uptake was observed for when SK-OV-3 (the negative control) cells were exposed to both 4T1 and BT-20 CLENs (FIGS. 2 and 3). Four different preparations of 4T1-CLENs all containing 25 mol % of cholesterol and different ratios of DPPE-PEG-$_{5000}$ were evaluated for cell uptake against the 4T1 cell line (FIG. 4). 4T1-CLENs containing 5 mol % of DPPE-PEG-$_{5000}$ demonstrated significant uptake compared to the other PEG-containing preparations (FIG. 4). In the next study, the optimized ratio of PEG-$_{5000}$ was used and compared the CLENs type to a nano-system with a lipid composition resembling Doxil (referred to here as Doxil$_{LP}$ (Doxil lipid preparation without doxorubicin)). The inclusion of DPPE-PEG-$_{5000}$ (5 mol %) significantly enhanced the cellular uptake of CLENs when compared to Doxil$_{LP}$ (FIG. 5).

Cytotoxicity Studies of Doxorubicin-Loaded CLENs

Figure 6:
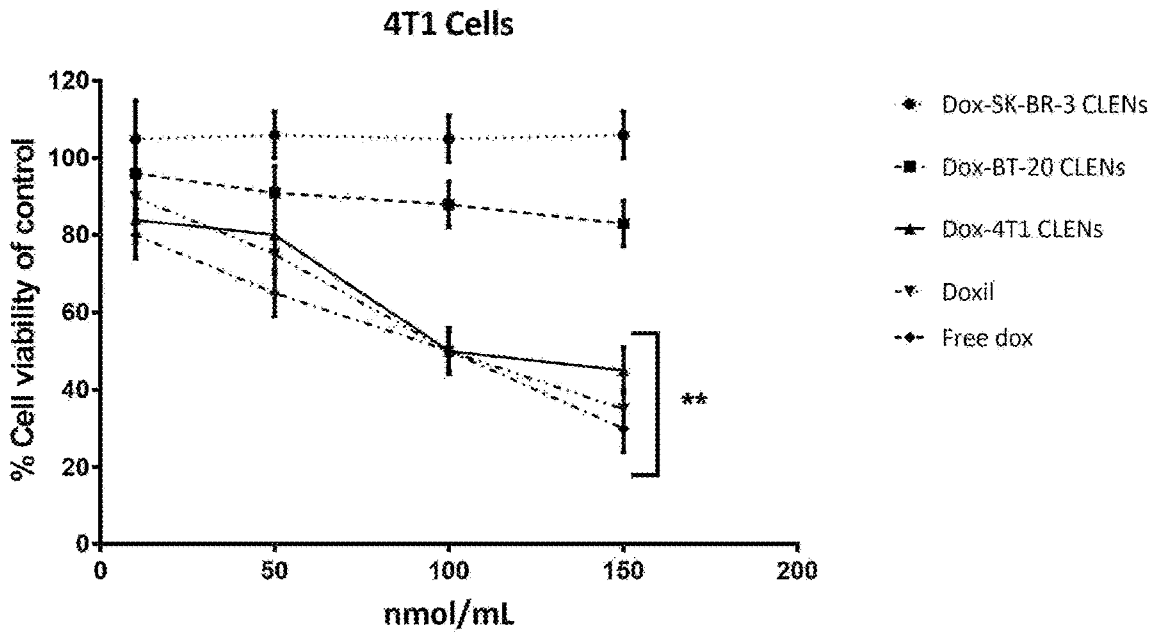
FIG. 6 shows exemplary cytotoxicity of doxorubicin-loaded CLENs. 4T1 cells were seeded at $1\times10^4$ per ml in a 48-well plate. Cells were exposed to different concentrations of doxorubicin-loaded CLENs (4T1, BT-20, and SKBR-3). SRB assay was used to determine percent of cell viability 24 hours following exposure to doxorubicin (5 mol %). Error bars indicate mean±S.D. (n=6).

Enhanced cellular uptake and selective drug targeting are important features of a drug delivery system, but how each translates overall to therapy is critical to success. For this reason, cytotoxicity of three different doxorubicin-loaded CLENs was evaluated for 4T1, BT-20 and SKBR-3 variety, doxil, and free doxorubicin (0.5 μmol/ml) against the growth of 4T1 cells in vitro. Results showed a significant decrease in the growth of 4T1 cells following exposure to 4T1 doxorubicin-loaded CLENs compared to untreated cells ($P<0.001$). The percent of viable cells was 50 and 46% for concentrations of 100 and 150 nmol/mL, respectively (FIG. 6). No significant difference in cytotoxicity was observed among 4T1 doxorubicin-loaded CLENs, doxil, and free doxorubicin. (FIG. 6). Interestingly, the non-specific SKBR-3 CLENs, for which similar amounts of drug agent was incorporated, was significantly less effective compared to 4T1 doxorubicin-loaded CLENs, doxil, and free doxorubicin (data not shown).

Discussion

Figure 7:
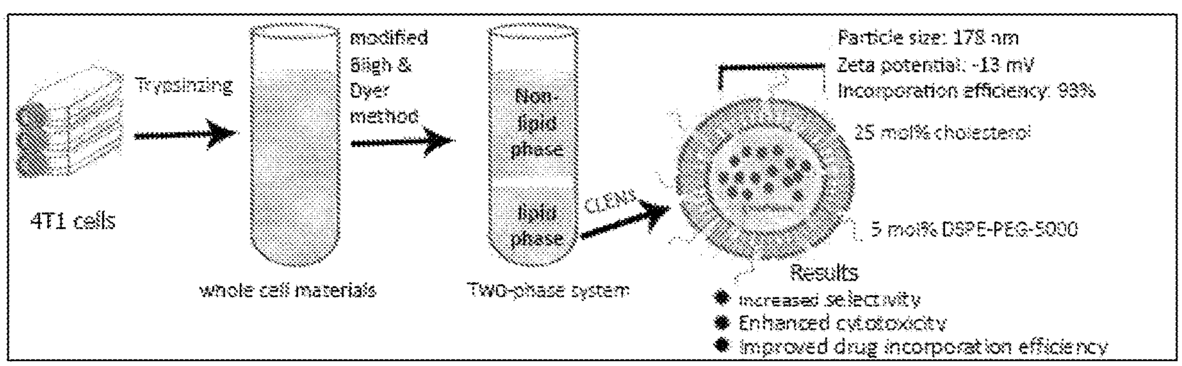
FIG. 7 is a schematic representation showing isolation of lipid extracts from target cells in preparation of CLENs. The schematic shows the process for preparing CLENs from isolation of the chloroform-soluble fraction which corresponds to the lipid extract phase mixture. The inclusion of cholesterol and DPPE-PEG5000 in CLENs improved drug incorporation, stability, cellular uptake, and cytotoxicity among other formulation properties.

Breast cancer is a major cause of cancer death in women worldwide (21-24). The disease is characterized by variant pathological features, disparate responses to therapeutics, and substantial differences in patient's long-term survival (13, 22, 24, 25). Targeted drug delivery systems (i.e., liposomes) can improve the pharmacokinetic and bio-distribution profile of commonly used drugs used for the treatment of disease (1, 3-5, 19, 26). Studies provided herein were performed to evaluate different nanoliposome formulations derived from natural lipid extracts from various breast cancer cell lines. Perhaps the lipid extracts could one day be optimized to target specific stages of tumor maturation and development. However, the general procedure employed for lipid extraction presented here was optimized for cell lines regardless of staging. Once the procedure was established no additional modifications made (FIG. 7). CLENs contain a wider range of different lipid components with varied acyl chain lengths and degree of unsaturation compared to more conventional liposomal preparations. In CLENs the lipids are naturally employed in ratios unique to the target cell, and the fractional makeup of the many different lipid components appears to make them less recognizable by non-target cell populations. This is ideal when selective drug targeting if needed.

Investigating the physicochemical characteristics of a drug carrier molecule is an important step to understanding formulation quality, stability, drug release rates and intracellular fate. The average particle size for CLENs was between 100-200 nm, the ideal size range for I.V. administered formulations (3-5, 27). The zeta potential values for CLENs were negatively-charged, suggesting the vehicle is likely to accumulate in the tumor interstitial environment following I.V. administration.(1, 5, 20, 27). Regardless of the cell type from which the CLENs were derived the CLENs were relatively non-toxic to target cells. This is not surprising given the similar composition profile between the target cell membrane and the nano delivery system.

In general, the most significant uptake was observed when the breast cancer (target) cells were exposed to CLENs prepared from lipids derived from the target cell. When the target cell population was exposed to lipid material from a different source the results were less impressive, suggesting the mechanism(s) underlying cellular uptake is a function of the lipid composition profile of CLENs, which is cell line-dependent (FIGS. 2 and 3).

The incorporation of chemotherapeutic agents in liposomes has been shown to enhance the therapeutic index of incorporated drug agents, either by increasing the drug concentration in tumor cells, or by decreasing exposure to normal healthy tissues (4, 12, 27).

Cholesterol and DPPE-PEG-$_{5000}$ are commonly used to optimize nanoliposome formulations (6, 9, 27). Cholesterol increases the packing order and the rigidity of liposomes. The decrease in the permeability of the lipid bilayer due to the inclusion of cholesterol has been shown to improve drug retention for various lipid-based nano-sized drug delivery systems.(28-30). PEGylation has offered opportunities to formulate drug carrier molecules that can evade opsonization and relatively rapid blood clearance (6, 27, 31). In our study, the inclusion of 5 mol % DPPE-PEG-$_{5000}$ in CLENs improved cellular uptake over other ratios evaluated (5 mol %>0, 2 and 10 mol % DPPE-PEG-$_{5000}$). The experimental finding is particularly noteworthy, suggesting a quite different role of PEG in CLENs compared to more conventional stealth liposomes. CLENs varied in the amount of drug incorporated. The most significant increase in incorporated drug was observed following the inclusion of 25 mol % cholesterol (86% drug loaded). The percent cholesterol is greater than that typically used to prepare conventional liposomes (28, 32, 33). Approximately 44% of drug was incorporated in CLENs consisting of 50 mol % cholesterol, the lowest percent of drug incorporated compared to others evaluated (Table 3; 25>10>0>50). Previously published reports support a correlation between relatively high cholesterol content and liposome instability (29, 34, 35). The optimal ratio of cholesterol with respect to conventional components employed is necessary; the balanced optimization will prevent premature drug release and instability.

Cellular uptake of CLENs by the target cells was greater than Doxil$_{LP}$. Moreover, 4T1 doxorubicin loaded-CLENs demonstrated more significant growth inhibitory effects. Data also support greater activity against intended target cells compared to non-specific target (control) cell populations. A greater degree of selectivity was observed when both the lipid extracts used to prepare CLENs and the target cell population were derived from the same organ tissue environment (i.e. breast). This result was highly consistent and reproducible. However, the most desirable results were achieved when CLENs were prepared directly from the target cell, when compared to cells that shared the organ tissue environment only (FIGS. 2 and 3).

Preliminary evaluation of the entire chloroform-soluble (lipid) fraction of 4T1 cells by LC/MS revealed a variety of glycosphingolipids among other lipid classes. Of interest, following evaluation of a different nanosystem composition, Pedrosa and colleagues showed that relatively short-chained glycosphingolipids (SC-GSLs) selectively entered target cell membranes when cells were exposed to SC-GSLs-modified liposomes. The authors suggested that the inclusion of SC-GSLs facilitated the transport of amphiphilic drugs (such as doxorubicin-hydrochloride) compared to non-glycosphingolipid-rich liposomes (36). Preliminary LC/MS studies confirm the presence of SC-GSLs in lipid extracts for 4T1, and in extracts derived from other organ tissues as well.

CONCLUSIONS

CLENs represent a novel nanoliposome drug platform capable of recognizing target cells with relatively high efficiency compared to more conventional nano-systems. The drug carrier was relatively non-toxic to cells when used at concentrations traditionally used to evaluate nanoparticles in vitro. Our studies collectively support the use of cellular membrane lipid extracts in combination with more conventional components of drug delivery systems to achieve more selective drug targeting. Overall, CLENs were most efficient when applied against intended target cell populations. However, the organ tissue environment appears to play a role in mechanism(s) underlying cell uptake. The results could thus vary depending on the host tissue environment.

REFERENCES

1. Campbell R B, Fukumura D, Brown E B, Mazzola L M, Izumi Y, et al. Cationic charge determines the distribution of liposomes between the vascular and extravascular compartments of tumors. Cancer Res. 2002; 62(23):6831-6.
2. Deshpande P P, Biswas S, Torchilin V P. Current trends in the use of liposomes for tumor targeting. Nanomedicine (Lond). 2013; 8(9):1509-28.
3. Torchilin V P. Recent advances with liposomes as pharmaceutical carriers. Nat Rev Drug Discov. 2005; 4(2): 145-60.
4. Sharma G, Anabousi S, Ehrhardt C, Ravi Kumar M N. Liposomes as targeted drug delivery systems in the treatment of breast cancer. J Drug Deliv. 2006; 14(5):301-10.
5. Campbell R B. Tumor physiology and delivery of nanopharmaceuticals. Anticancer agents med chem. 2006; 6(6):503-12.
6. Sadzuka Y, Kishi K, Hirota S, Sonobe T. Effect of polyethyleneglycol (PEG) chain on cell uptake of PEG-modified liposomes. J liposome res. 2003; 13(2):157-72.
7. Dan N. Effect of liposome charge and PEG polymer layer thickness on cell-liposome electrostatic interactions. Biochim Biophys acta. 2002; 1564(2):343-8.
8. Eloy J O, Claro de Souza M, Petrilli R, Barcellos J P, Lee R J, et al. Liposomes as carriers of hydrophilic small molecule drugs: Strategies to enhance encapsulation and delivery. Colloids Surf B Biointerfaces. 2014; 123c:345-63.
9. Hatakeyama H, Akita H, Harashima H. The polyethyleneglycol dilemma: advantage and disadvantage of PEGylation of liposomes for systemic genes and nucleic acids delivery to tumors. Biol Pharm Bull. 2013; 36(6): 892-9.
10. Jain A, Jain S K. PEGylation: an approach for drug delivery. A review. Crit Rev Ther Drug Carrier Syst. 2008; 25(5):403-47.
11. Ryan S M, Mantovani G, Wang X, Haddleton D M, Brayden D J. Advances in PEGylation of important biotech molecules: delivery aspects. Expert Opin Drug Deliv. 2008; 5(4):371-83.
12. Vemuri S, Rhodes C T. Preparation and characterization of liposomes as therapeutic delivery systems: a review. Pharm Acta Helv. 1995; 70(2):95-111.
13. Verma S, Dent S, Chow B J, Rayson D, Safra T. Metastatic breast cancer: the role of pegylated liposomal doxorubicin after conventional anthracyclines. Can treat rev. 2008; 34(5):391-406.
14. Lu Y, Low P S. Folate-mediated delivery of macromolecular anticancer therapeutic agents. Adv Drug Deliv Rev. 2002; 54(5):675-93.
15. Mathias C J, Wang S, Waters D J, Turek J J, Low P S, et al. Indium-111-DTPA-folate as a potential folate-receptor-targeted radiopharmaceutical. J nuc med. 1998; 39(9): 1579-85.
16. Bligh E G, Dyer W J. A rapid method of total lipid extraction and purification. Can J biochem phys. 1959; 37(8):911-7.
17. Dabbas S, Kaushik R R, Dandamudi S, Kuesters G M, Campbell R B. Importance of the liposomal cationic lipid content and type in tumor vascular targeting: physicochemical characterization and in vitro studies using human primary and transformed endothelial cells. Endothelium. 2008; 15(4):189-201.
18. Dandamudi S, Campbell R B. The drug loading, cytotoxicty and tumor vascular targeting characteristics of magnetite in magnetic drug targeting. Biomaterials. 2007; 28(31):4673-83.
19. Kalra A V, Campbell R B. Development of 5-FU and doxorubicin-loaded cationic liposomes against human pancreatic cancer: Implications for tumor vascular targeting. Pharm res. 2006; 23(12):2809-17.
20. DeSantis C, Ma J, Bryan L, Jemal A. Breast cancer statistics, 2013. CA Cancer J Clin. 2014; 64(1):52-62.
21. Hassan M S, Ansari J, Spooner D, Hussain S A. Chemotherapy for breast cancer (Review). Onco rep. 2010; 24(5):1121-31.
22. Jemal A, Bray F, Center M M, Ferlay J, Ward E, Forman D. Global cancer statistics. C A. 2011; 61(2):69-90.
23. Moulder S, Hortobagyi G N. Advances in the treatment of breast cancer. Clin pharm thera. 2008; 83(1):26-36.
24. Rivenbark A G, O'Connor S M, Coleman W B. Molecular and cellular heterogeneity in breast cancer: challenges for personalized medicine. Am J Path. 2013; 183(4):1113-24.
25. Taylor K M G, Taylor G, Kellaway I W, Stevens J. Drug entrapment and release from multilamellar and reverse-phase evaporation liposomes. Inter J Pharma. 1990; 58(1): 49-55.
26. Allen T M, Hansen C, Martin F, Redemann C, Yau-Young A. Liposomes containing synthetic lipid derivatives of poly(ethylene glycol) show prolonged circulation half-lives in vivo. Biochem biophys acta. 1991; 1066(1): 29-36.
27. Pasenkiewicz-Gierula M, Rog T, Kitamura K, Kusumi A. Cholesterol effects on the phosphatidylcholine bilayer polar region: a molecular simulation study. Biophys J. 2000; 78(3):1376-89.
28. Raffy S, Teissié J. Control of lipid membrane stability by cholesterol content. Biophys J. 1999; 76(4):2072-80.
29. Tseng L P, Liang H J, Chung T W, Huang Y Y, Liu D Z. Liposomes incorporated with cholesterol for drug release triggered by magnetic field. J Med Bio Eng. 2007; 27(1): 29-34.
30. Sadzuka Y, Sugiyama I, Tsuruda T, Sonobe T. Characterization and cytotoxicity of mixed polyethyleneglycol modified liposomes containing doxorubicin. Inter J pharma. 2006; 312(1-2):83-9.
31. Drummond D C, Meyer O, Hong K, Kirpotin D B, Papahadjopoulos D. Optimizing liposomes for delivery of chemotherapeutic agents to solid tumors. Pharmacol Rev. 1999; 51(4):691-743.
32. Ohvo-Rekila H, Ramstedt B, Leppimaki P, Slotte J P. Cholesterol interactions with phospholipids in membranes. Prog lipid res. 2002; 41(1):66-97.
33. Cui Z K, Edwards K, Orellana A N, Bastiat G, Benoit J P, Lafleur M. Impact of interfacial cholesterol-anchored polyethylene glycol on sterol-rich non-phospholipid liposomes. J colloid inter sci. 2014; 428:111-20.
34. Decker C, Fahr A, Kuntsche J, May S. Selective partitioning of cholesterol and a model drug into liposomes of varying size. Chem phys lipids. 2012; 165(5):520-9.
35. Pedrosa L R, Ten Hagen T L, Suss R, van Hell A, Eggermont A M, Verheij M, et al. Short-chain glycoceramides promote intracellular mitoxantrone delivery from novel nanoliposomes into breast cancer cells. Pharma res. 2015; 32(4):1354-67.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one or all of the group members are present in, employed in or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of making a nanoliposome comprising a chemotherapeutic agent, the method comprising the steps of:

(i) isolating a cell membrane from a tumor cell, (ii) performing solvent extraction to separate a lipid phase from a non-lipid phase, wherein the non-lipid phase includes proteins, (iii) isolating the lipid phase, (iv) preparing the nanoliposome from lipids of the lipid phase, and further comprising contacting the lipids of the lipid phase with cholesterol and/or polyethylene glycol (PEG) to produce a lipid mixture, and (v) contacting the lipids with a chemotherapeutic agent, thereby producing a nanoliposome comprising the chemotherapeutic agent.

2. The method of claim 1, wherein the solvent extraction comprises chloroform extraction.

3. The method of claim 1, wherein the solvent extraction comprises chloroform-methanol extraction.

4. The method of claim 1, wherein the cell membrane is a plasma cell membrane.

5. The method of claim 1, wherein the method further comprises subjecting the lipid phase to lyophilization.

6. The method of claim 1, wherein the method further comprises contacting the lipids of the lipid phase with cholesterol to produce a lipid mixture.

7. The method of claim 6, wherein lipid mixture comprises from 1 to 50 mol % of cholesterol.

8. The method of claim 6, wherein the method further comprises contacting the lipid mixture with polyethylene glycol (PEG).

9. The method of claim 8, wherein lipid mixture comprises from 1 to 20 mol % of PEG.

10. The method of claim 8, wherein lipid mixture comprises from 1 to 10 mol % of PEG.

11. The method of claim 9, wherein the PEG comprises DPPE-PEG-5000.

12. The method of claim 1, wherein the nanoliposome is prepared from the lipids of the lipid phase in step (iv) by a reverse phase evaporation method with a lipid composition comprising phosphatidylcholine, cholesterol and PEG-derivatized phosphatidylethanolamine (PEG-PE).

13. The method of claim 1, wherein the nanoliposome is prepared from the lipids of the lipid phase in step (iv) by a thin film hydration method.

14. The method of claim 1, wherein the tumor cell is isolated from a subject having cancer, optionally breast cancer.

15. The method of claim 1, wherein the tumor cell is a cell from a cell line grown in cell culture, optionally a cell line selected from the group consisting of 4T1, a BT-20, SK-BR-3, and SK-OV-3.

16. The method of claim 1, wherein the nanoliposome has a diameter ranging from 100 nm to 400 nm or 150 nm to 263 nm.

17. The method of claim 1, wherein the nanoliposome is prepared from the lipids of the lipid phase in step (iv) by extruding the lipids through filters of defined pore size to yield liposomes with a set diameter.

* * * * *